United States Patent
Yang et al.

(10) Patent No.: US 9,175,014 B2
(45) Date of Patent: Nov. 3, 2015

(54) METHOD FOR PREPARING CU-BTC AND NANO-CU-BTC

(71) Applicants: NANJING TECH UNIVERSITY, Nanjing (CN); CHANGSHU YUTYRONE ADVANCED WEAR MATERIALS TECHNOLOGY CO., LTD., Changshu (CN)

(72) Inventors: Zhuhong Yang, Nanjing (CN); Hong Liu, Nanjing (CN); Suoying Zhang, Nanjing (CN); Wenjun Yao, Changshu (CN); Xiaohua Lu, Nanjing (CN); Changsong Wang, Nanjing (CN)

(73) Assignees: NANJING TECH UNIVERSITY, Nanjing (CN); CHANGSHU YUTYRONE ADVANCED WEAR MATERIALS TECHNOLOGY CO., LTD., Changshu (CN)

( * ) Notice: Subject to any disclaimer, the term of this patent is extended or adjusted under 35 U.S.C. 154(b) by 0 days.

(21) Appl. No.: 14/427,911

(22) PCT Filed: Oct. 10, 2012

(86) PCT No.: PCT/CN2012/082728
§ 371 (c)(1),
(2) Date: Mar. 12, 2015

(87) PCT Pub. No.: WO2014/056166
PCT Pub. Date: Apr. 17, 2014

(65) Prior Publication Data
US 2015/0259360 A1 Sep. 17, 2015

(51) Int. Cl.
*C07F 1/08* (2006.01)

(52) U.S. Cl.
CPC .................................. *C07F 1/08* (2013.01)

(58) Field of Classification Search
CPC ................................. C07F 1/08; C07C 51/418
USPC ............................................................ 556/115
See application file for complete search history.

(56) References Cited

U.S. PATENT DOCUMENTS

| | | | |
|---|---|---|---|
| 2009/0042000 A1* | 2/2009 | Schubert | C07C 51/418 428/219 |
| 2014/0284829 A1* | 9/2014 | Maspoch Comamala | B01J 31/16 264/12 |
| 2015/0175518 A1* | 6/2015 | Schroder | C01B 37/00 556/115 |

FOREIGN PATENT DOCUMENTS

| | | |
|---|---|---|
| CN | 101384537 | 3/2009 |
| WO | 2012/131483 A1 | 10/2012 |

* cited by examiner

*Primary Examiner* — Porfirio Nazario Gonzalez
(74) *Attorney, Agent, or Firm* — CBM Patent Consulting, LLC

(57) ABSTRACT

The methods for preparing Cu-BTC and nano-Cu-BTC are disclosed. An imporous coordination compound $Cu(C_9H_4O_6)(H_2O)_3$ is impregnated an organic solvent or a steam environment thereof to obtain Cu-BTC. Cu-BTC is impregnated in an acidic protic solvent environment and filtered to obtain a solid, and the solid is impregnated in a non-acidic organic solvent or a steam environment thereof, centrifuged, washed, and dried, to obtain nano-Cu-BTC.

13 Claims, 2 Drawing Sheets

METHOD FOR PREPARING CU-BTC AND NANO-CU-BTC

This application is the U.S. national phase of International Application No. PCT/CN2012/082728 filed on 10 Oct. 2012 which designated the U.S., the entire content of the International Application hereby incorporated by reference.

TECHNICAL FIELD

The present invention relates to methods for preparing Cu-BTC and nano-Cu-BTC.

RELATED ART

Metal organic frameworks (MOFs) are porous materials having a periodic network structure formed by metal ions or clusters and organic ligands through self-assembly, have the advantages of large specific surface area, high porosity, and adjustable structure, are considered as the most promising materials for gas adsorption, catalysis and sensing, and have attracted extensive attention in recent years.

Since being prepared, Cu-BTC has been widely studied. Cu-BTC has the characteristics of unsaturated metal sites and a paddle wheel structure. As the most well-known MOF material, Cu-BTC has been commercialized, but the price is high. The reason lies in that the main method for synthesizing Cu-BTC is a solvothermal method, which is time consuming and has high energy costs. In recent years, due the emergence of microwave and ultrasound methods, the time for synthesizing MOFs material are reduced, the reaction energy consumption is reduced, but due to the limitation of equipment, these methods are difficult to be industrially scaled up. At the same time, due to the unique dimension effects and interface effects, nano materials have been a hot research spot. nano-scaled Cu-BTC can not only significantly increase the diffusion rate of gas, improve the adsorption and separation and the catalytic performance of materials, but also can improve the response of the materials to applied optical, electrical, temperature and pressure fields, thus expanding its application in the sensing field. Currently, the nano-scaled Cu-BTC is mainly prepared by emulsion and template methods, the process is complex, the conditions are harsh, and the costs are high.

In view of this research status, the present invention set forth methods for rapidly preparing Cu-BTC and a nano-Cu-BTC material at normal temperature and normal pressure.

SUMMARY

In view of the problems that the existing method for preparing a Cu-BTC material is time consuming and energy consuming, and the process for preparing nano-Cu-BTC is complex, the present invention provides a method for Cu-BTC and a nano-Cu-BTC material at normal temperature and normal pressure.

The present invention can be achieved through the following measures:

A method for preparing Cu-BTC is provided, including: impregnating $Cu(C_9H_4O_6)(H_2O)_3$ in an organic solvent or an organic solvent steam, reacting with stirring, washing, filtering and drying, to obtain Cu-BTC. Cu-BTC prepared by this method is a three-dimensional porous coordination compound having a specific surface area of greater than 600 $m^2/g$, and has a structure the same as that prepared by other methods in the prior art.

$Cu(C_9H_4O_6)(H_2O)_3$ is a whisker-shaped imporous coordination compound having XRD characteristic peaks at $2\theta$ of 9.4, 11.35, 13.95, 16.2, 16.85, 17, 18.75, 19.45. The method for preparing $Cu(C_9H_4O_6)(H_2O)_3$ is known to those of ordinary skill in the art, and includes reacting an aqueous solution of perchloric acid with an ethanol solution of trimesic acid ($H_3BTC$) (ActaCryst., 1988, C44. 992-994), and the prepared $Cu(C_9H_4O_6)(H_2O)_3$ generally has a specific surface area of less than 200 $m^2/g$.

The organic solvent is preferably at least one of methanol, ethanol, N,N-dimethylformamide (DMF), dimethyl sulfoxide, acetonitrile, sulfolane, acetone, dimethylacetamide and hexamethylphosphoramide.

The solid-liquid ratio of $Cu(C_9H_4O_6)(H_2O)_3$ to the organic solvent is 1 g/L to 100 g/L; and the duration of the reaction is 1 to 60 min.

A method for preparing nano-Cu-BTC is provided, including: impregnating Cu-BTC in an acidic protic solvent environment and filtered to obtain a solid, impregnating the solid in a non-acidic organic solvent or a steam environment of a non-acidic organic solvent, centrifuged, washed, and dried, to obtain nano-Cu-BTC. The raw material Cu-BTC useful in this method may be commercially available Cu-BTC, and may also be Cu-BTC prepared by the method of the present invention. The cost can be reduced by using Cu-BTC prepared by the method of the present invention.

The acidic protic solvent in the present invention refers to a protic solvent having a pH of less than 7. The concentration of the acidic protic solvent is pH=1 to 3. When the pH is excessively low, the acidity is excessively strong, and the structure of Cu-BTC may be decomposed; when the pH value is excessively high, nano-Cu-BTC cannot be prepared.

The solid-liquid ratio of Cu-BTC to the acidic protic solvent is 1 g/L to 50 g/L; Cu-BTC is impregnated in an acidic protic solvent or a non-acidic organic solvent for a duration of 1 min to 600 min; and preferably, for a duration of 1 min to 100 min, respectively.

The acidic protic solvent includes all strong acids, and is preferably at least one of formic acid, hydrochloric acid, sulfuric acid, nitric acid, hydroiodic acid, hydrobromic acid, perchloric acid and chloric acid.

Cu-BTC is prepared by the method below: impregnating $Cu(C_9H_4O_6)(H_2O)_3$ in an organic solvent or an organic solvent steam, reacting with stirring, washing, filtering and drying, to obtain Cu-BTC.

$Cu(C_9H_4O_6)(H_2O)_3$ is a whisker-shaped imporous coordination compound having XRD characteristic peaks at $2\theta$ of 9.4, 11.35, 13.95, 16.2, 16.85, 17, 18.75, 19.45.

The solid-liquid ratio of $Cu(C_9H_4O_6)(H_2O)_3$ to the organic solvent is 1 g/L to 100 g/L; and the duration of the reaction is 1 to 60 min.

The non-acidic organic solvent useful in preparing nano-Cu-BTC refers to an organic solvent having a pH value of greater than 7, and the non-acidic organic solvent is preferably at least one of methanol, ethanol, N,N-dimethylformamide, dimethyl sulfoxide, acetonitrile, sulfolane, acetone, dimethylacetamide and hexamethylphosphoramide.

The organic solvent useful in preparing Cu-BTC is preferably at least one of methanol, ethanol, N,N-dimethylformamide, dimethyl sulfoxide, acetonitrile, sulfolane, acetone, dimethylacetamide and hexamethylphosphoramide.

The methods for preparing Cu-BTC and nano-Cu-BTC of the present invention are carried out under moderate reaction conditions at normal temperature and normal pressure. In the present invention, the normal temperature is 2° C. 0 to 30° C., and the normal pressure is generally 100 KPa to 101 KPa.

Compared with conventional methods, the present invention has the following beneficial effects:

1. The present invention has the advantage that the reaction conditions for preparing Cu-BTC and nano-Cu-BTC are moderate, the process energy consumption is low, the reactions are rapid, the raw materials are commonly inexpensive industrial solvents, and the preparation costs are low.
2. The present invention has the advantage that the reactions for preparing Cu-BTC and nano-Cu-BTC are simple, the required equipment is simple, and large scale production can be easily carried out.
3. The present invention has the advantage that the size of nano-Cu-BTC can be adjusted by controlling the number of cycle operations of preparation of nano-Cu-BTC.
4. The present invention has the advantage that the preparation of three-dimensional porous nano-Cu-BTC from a nonporous whisker-shaped compound has significant meaning for development of advanced functional materials.

BRIEF DESCRIPTION OF THE DRAWINGS

The disclosure will become more fully understood from the detailed description given herein below for illustration only, and thus are not limitative of the disclosure, and wherein.

DETAILED DESCRIPTION

The present invention is further described below with reference to the following embodiment.

In the following implementation, the experimental methods are conventional methods unless otherwise stated; all reagents or raw materials are commercially available unless otherwise stated.

Embodiment 1

Preparation of $Cu(C_9H_4O_6)(H_2O)_3$

At normal temperature and normal pressure, 15 ml deionized water with 2 g $Cu(ClO_4)_2$ dissolved therein and 15 ml ethanol solution with 1 g trimesic acid dissolved therein were mixed and reacted for 3 h with stiffing, to obtain $Cu(C_9H_4O_6)(H_2O)_3$.

Embodiment 2

At normal temperature and normal pressure, 1 g $Cu(C_9H_4O_6)(H_2O)_3$ was impregnated in 20 ml DMF solvent and reacted for 3 min with stirring to obtain a precipitate. The precipitate was washed, filtered and dried, to obtain Cu-BTC. The yield was 92.56% (based on trimesic acid). The resulting sample was subjected to SEM ad XRD for characterization.

Figure 1:
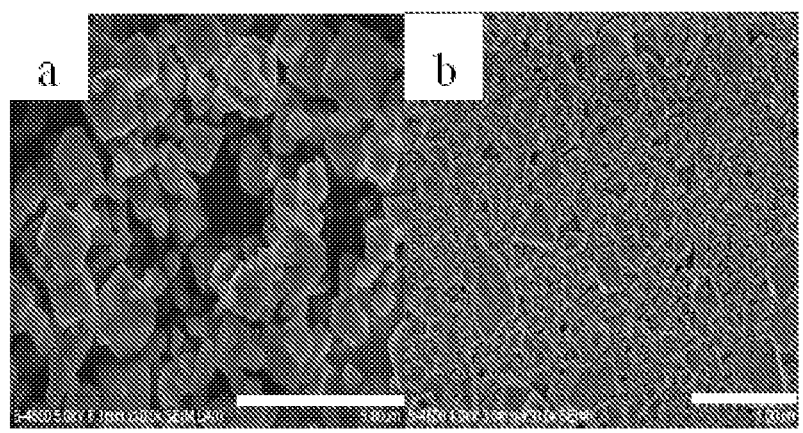
FIG. 1 shows scanning electron micrographs of (SEM) of Cu-BTC prepared in Embodiment 2 and nano-Cu-BTC Embodiment 8,
a) Prepared Cu-BTC; b) Prepared nano-Cu-BTC.
Figure 2:
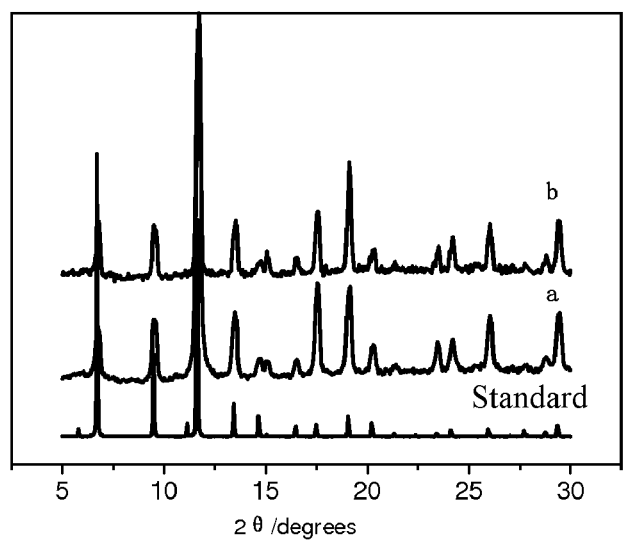
FIG. 2 shows powder X-ray diffraction patterns (XRD) of Cu-BTC prepared in Embodiment 2 and nano-Cu-BTC Embodiment 8,
a) Prepared Cu-BTC; b) Prepared nano-Cu-BTC.

The XRD pattern of the resulting Cu-BTC is shown in FIG. 2, and is fully consistent with the standard pattern, indicating that the Cu-BTC prepared by this method has high degree of crystallinity and high purity.

Embodiments 3 to 7

Embodiments 3 to 7 were carried out according to the steps in Embodiment 2, to prepare Cu-BTC.

The specific reaction principles, conditions and the yield of Cu-BTC are shown in Table 1.

TABLE 1

Raw materials and preparation conditions of Embodiments 3 to 7

| Other embodiments | Control conditions | | | Yield of Cu-BTC |
|---|---|---|---|---|
| | $Cu(C_9H_4O_6)(H_2O)_3$/ organic solvent (g/L) | Organic solvent | Duration min | |
| Embodiment 3 | 50 | dimethyl sulfoxide | 1 | 90.43% |
| Embodiment 4 | 10 | methanol steam | 30 | 91.38% |
| Embodiment 5 | 30 | ethanol | 15 | 93.41% |
| Embodiment 6 | 20 | sulfolane | 10 | 90.88% |
| Embodiment 7 | 30 | acetone | 8 | 91.45% |

Embodiment 8

1 g Cu-BTC was impregnated in 50 ml hydrochloric acid solution at pH=1.5 and reacted for 10 min with stiffing, and filtered to obtain a solid. The solid was impregnated in 50 ml N,N-dimethylformamide solution and reacted for 5 min with stirring, filtered, washed and dried, to obtain nano-Cu-BTC. The yield was 85%. The resulting sample was subjected to SEM ad XRD for characterization. The resulting nano-Cu-BTC particles had an average size of 573 nm.

Embodiments 9 to 15

Embodiments 9 to 15 were carried out according to the steps in Embodiment 8, and the raw materials and conditions for specific reactions and particle size of the product were shown in Table 1.

TABLE 1

Raw materials and preparation conditions in Embodiments 9 to 15

| Other embodiments | Control conditions | | | | | | Structure and properties Average size of Cu-BTC nm |
|---|---|---|---|---|---|---|---|
| | Cu-BTC/Acid solution(g/L) | Acid solution | pH value of the solution | Duration min | Non-acidic organic solution | Duration min | |
| Embodiment 9 | 50 | nitric acid | 1 | 3 | dimethyl sulfoxide | 3 | 511 |
| Embodiment 10 | 10 | sulfuric acid | 3 | 10 | methanol steam | 5 | 625 |
| Embodiment 11 | 30 | hydrochloric acid | 1 | 5 | ethanol | 15 | 457 |
| Embodiment 12 | 20 | nitric acid | 2 | 5 | sulfolane | 10 | 610 |
| Embodiment 13 | 30 | hydroiodic acid, | 3 | 3 | acetone | 8 | 568 |

TABLE 1-continued

Raw materials and preparation conditions in Embodiments 9 to 15

| Other embodiments | Control conditions | | | | | | Structure and properties Average size of Cu-BTC nm |
|---|---|---|---|---|---|---|---|
| | Cu-BTC/Acid solution(g/L) | Acid solution | pH value of the solution | Duration min | Non-acidic organic solution | Duration min | |
| Embodiment 14 | 20 | formic acid | 2 | 8 | dimethylacetamide | 10 | 636 |
| Embodiment 15 | 100 | perchloric acid | 1.5 | 5 | hexamethylphosphoramide | 8 | 570 |

Comparative Example 1

1 g Cu-BTC was impregnated in 50 ml hydrochloric acid solution at pH=0 and reacted for 5 min with stirring, and filtered to obtain a white solid. The solid was impregnated in 50 ml N,N-dimethylformamide solution and reacted for 5 min with stirring till the white solid was not changed, filtered, washed and dried, to obtain a product. The product was not Cu-BTC.

Comparative Example 2

1 g Cu-BTC was impregnated in 50 ml hydrochloric acid solution at pH=4 and reacted for 10 min with stiffing, and filtered to obtain a solid. The solid was impregnated in 50 ml N,N-dimethylformamide solution and reacted for 5 min with stirring, filtered, washed and dried, to obtain a Cu-BTC, where the product had an average particle diameter of 437 μm.

Comparative Examples 1 and 2 indicate that when the acidity of the used protic solvent is excessively strong or weak, nano-Cu-BTC cannot be prepared. When the acidity is excessively strong, Cu-BTC is directly decomposed; when the acidity is excessively weak, nano-Cu-BTC cannot be prepared.

What is claimed is:

1. A method for preparing Cu-BTC, comprising: impregnating $Cu(C_9H_4O_6)(H_2O)_3$ in an organic solvent or an organic solvent steam, reacting with stifling, washing, filtering and drying, to obtain Cu-BTC.

2. The method according to claim 1, wherein $Cu(C_9H_4O_6)(H_2O)_3$ is a whisker-shaped imporous coordination compound having XRD characteristic peaks at 2θ of 9.4, 11.35, 13.95, 16.2, 16.85, 17, 18.75, 19.45.

3. The method according to claim 1, wherein the organic solvent comprises at least one of methanol, ethanol, N,N-dimethylformamide, dimethyl sulfoxide, acetonitrile, sulfolane, acetone, dimethylacetamide and hexamethylphosphoramide.

4. The method according to claim 1, wherein the solid-liquid ratio of $Cu(C_9H_4O_6)(H_2O)_3$ to the organic solvent is 1 g/L to 100 g/L; and the duration of the reaction is 1 to 60 min.

5. A method for preparing nano-Cu-BTC, comprising: impregnating Cu-BTC in an acidic protic solvent environment and filtered to obtain a solid, impregnating the solid in a non-acidic organic solvent or a steam environment of a non-acidic organic solvent, centrifuged, washed, and dried, to obtain nano-Cu-BTC.

6. The method according to claim 5, wherein the concentration of the acidic protic solvent is pH=1 to 3.

7. The method according to claim 5, wherein the solid-liquid ratio of Cu-BTC to the acidic protic solvent is 1 g/L to 50 g/L; Cu-BTC is impregnated in the acidic protic solvent or non-acidic organic solvent for a duration of 1 min to 600 min, and preferably, for a duration of 1 min to 100 min.

8. The method according to any one of claims 5 to 7, wherein the acidic protic solvent comprises all strong acids; and is preferably at least one of formic acid, hydrochloric acid, sulfuric acid, nitric acid, hydroiodic acid, hydrobromic acid, perchloric acid and chloric acid.

9. The method according to claim 5, wherein Cu-BTC is prepared by using the method below: impregnating $Cu(C_9H_4O_6)(H_2O)_3$ in an organic solvent or an organic solvent steam, reacting with stifling, washing, filtering and drying, to obtain Cu-BTC.

10. The method according to claim 9, wherein $Cu(C_9H_4O_6)(H_2O)_3$ is a whisker-shaped imporous coordination compound having XRD characteristic peaks at 2θ of 9.4, 11.35, 13.95, 16.2, 16.85, 17, 18.75, 19.45.

11. The method according to claim 5, wherein the solid-liquid ratio of $Cu(C_9H_4O_6)(H_2O)_3$ to the organic solvent is 1 g/L to 100 g/L; and the duration of the reaction is 1 to 60 min.

12. The method according to claim 5 or 7, wherein the non-acidic organic solvent comprises at least one of methanol, ethanol, N,N-dimethylformamide, dimethyl sulfoxide, acetonitrile, sulfolane, acetone, dimethylacetamide and hexamethylphosphoramide.

13. The method according to claim 9 or 11, wherein the organic solvent comprises at least one of methanol, ethanol, N,N-dimethylformamide, dimethyl sulfoxide, acetonitrile, sulfolane, acetone, dimethylacetamide and hexamethylphosphoramide.

* * * * *